(12) United States Patent
Minato et al.

(10) Patent No.: US 6,891,080 B2
(45) Date of Patent: May 10, 2005

(54) DISPOSABLE DIAPER AND ABSORBENT MEMBER USED THEREIN

(75) Inventors: Masanori Minato, Haga-gun (JP); Shigeto Yanagihara, Haga-gun (JP); Kenji Ishiguro, Haga-gun (JP); Mikio Suzuki, Haga-gun (JP); Tetsuya Masuki, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/443,990

(22) Filed: May 23, 2003

(65) Prior Publication Data

US 2003/0208174 A1 Nov. 6, 2003

Related U.S. Application Data

(62) Division of application No. 09/869,708, filed as application No. PCT/JP00/02328 on Apr. 10, 2000, now Pat. No. 6,649,810.

(30) Foreign Application Priority Data

Apr. 12, 1999 (JP) ............................................. 11-104626
Apr. 12, 1999 (JP) ............................................. 11-104627
Apr. 12, 1999 (JP) ............................................. 11-104628
May 14, 1999 (JP) ............................................. 11-134310

(51) Int. Cl.$^7$ ............................................... A61F 13/15
(52) U.S. Cl. .................................................... 604/368
(58) Field of Search ................................. 604/364, 367, 604/368, 374, 377, 378

(56) References Cited

U.S. PATENT DOCUMENTS

| | | | | |
|---|---|---|---|---|
| 4,327,728 A | * | 5/1982 | Elias ........................... | 604/368 |
| 4,818,534 A | * | 4/1989 | Levy ............................ | 424/404 |
| 4,822,668 A | * | 4/1989 | Tanaka et al. ................ | 428/283 |
| 5,516,569 A | | 5/1996 | Veith et al. | |
| 5,749,863 A | | 5/1998 | Payne | |
| 5,836,929 A | | 11/1998 | Bewick-Sonntag et al. | |
| 5,843,063 A | | 12/1998 | Anderson et al. | |
| 6,072,101 A | * | 6/2000 | Beihoffer et al. ............ | 604/372 |
| 6,218,593 B1 | * | 4/2001 | Torimae et al. ............. | 604/366 |
| 6,632,974 B1 | * | 10/2003 | Suzuki et al. ................ | 604/369 |
| 6,649,810 B1 | * | 11/2003 | Minato et al. ............... | 604/379 |

FOREIGN PATENT DOCUMENTS

| | | | | |
|---|---|---|---|---|
| CN | 1044470 A | | 8/1990 | |
| CN | 1134271 A | | 10/1996 | |
| EP | 0401189 A1 | | 12/1990 | |
| EP | 0 526225 A1 | | 2/1993 | |
| EP | 0700672 A | | 3/1996 | |
| EP | 0719531 A1 | | 7/1996 | |
| GB | 2 284 551 A | | 6/1995 | |
| JP | 5-212072 A | | 8/1993 | |
| JP | 405228172 A | * | 9/1993 | ............ A61F/13/15 |
| JP | 406098909 A | * | 4/1994 | ............ A61F/13/15 |
| JP | 406315502 A | * | 11/1994 | ............ A61F/13/15 |
| JP | 10-118117 A | * | 5/1998 | ............ A61F/13/15 |
| WO | WO 90/08806 A1 | | 8/1990 | |
| WO | WO 91/11164 A | | 8/1991 | |
| WO | WO 96/17681 | * | 6/1996 | ............ B01J/20/00 |
| WO | WO 97/05841 A1 | | 2/1997 | |

* cited by examiner

Primary Examiner—Larry I. Schwartz
Assistant Examiner—Michael G. Bogart
(74) Attorney, Agent, or Firm—Birch, Stewart, Kolasch & Birch, LLP

(57) ABSTRACT

A disposable diaper is provided comprising a liquid permeable topsheet, a liquid impermeable backsheet, and a liquid retentive absorbent member interposed between the topsheet and the backsheet. The absorbent member comprises, in admixture, a superabsorbent polymer A having a rate of absorption of 8 g/30 sec/0.3 g or more measured by DW method and a superabsorbent polymer B having a rate of absorption of 5 g/30 sec/0.3 g or less measured by DW method at a polymer A/polymer B weight ratio of 90/10 to 10/90. The admixture optionally further comprises fluff pulp in an amount of from 0 to 30% by weight.

6 Claims, 3 Drawing Sheets

DISPOSABLE DIAPER AND ABSORBENT MEMBER USED THEREIN

This application is a divisional of application Ser. No. 09/869,708, filed on Jul. 12, 2001 now U.S. Pat. No. 6,649,810 for which priority is claimed under 35 U.S C. §120. application Ser. No. 09/869,708 is the national phase of PCT International Application No. PCTVJP00/02328 filed on Apr. 10, 2000 under 35 U.S.C. §371. The entire contents of each of the above-identified applications are hereby incorporated by reference. This application also claims priority of Application Nos. 11-104626, 11,104627, 11-104628 and 11-134310 filed in Japan on Apr. 12, 1999, Apr. 12, 1999, Apr. 12, 1999 and May 14, 1999 under 35 U.S.C. §119.

TECHNICAL FIELD

The present invention relates to disposable diapers which are light and compact and easy to carry around even when bunched up in a package and which are excellent in leakproofness.

The present invention also relates to absorbent articles, such as disposable diapers, which are light and yet has a moderate thickness to secure an easy feeling while in use.

BACKGROUND ART

Improvements have been added to the structure and materials of disposable diapers to provide compact packages convenient to carry.

However, packages containing several disposable diapers now on the market are still fairly heavy, some exceeding 3 kg, and carrying a package has been a considerable burden.

It is a conceivable solution for lightening a package of disposable diapers to decrease the number of disposable diapers per package, but such reduces distribution efficiency, incurring an increase of unit price and increasing the frequency of consumer purchases.

Mere cutting down the absorbent material to reduce the weight of individual disposable diapers would result in frequent leaks, making the diapers useless.

If absorbent articles such as disposable diapers are made thinner to make the package more compact, the absorbent article feels flimsy and makes a user feel a fear of leakage. Japanese Patent Laid-Open No. 212072/93 discloses a technique in which an ultrathin functional absorbent member is used while securing some thickness by a combined use of a bulk layer. According to this technique, it is possible to provide an absorbent article which comprises an ultrathin absorbent member and yet gives easy feelings, but the package is not at all compact.

DISCLOSURE OF THE INVENTION

Accordingly, a primary object of the present invention is to provide a disposable diaper which is light and compact and convenient to carry even when a plurality of the disposable diapers are packaged together and also which is excellent in leakproofness.

A secondary object of the present invention is to provide an absorbent article which is reduced in thickness and made more compact in a packaged state and restores its thickness on being taken out of the package for use thereby to make a user feel at ease while in use and which has cushioning to provide a good fit to a wearer on putting on.

The primary object of the present invention is accomplished by providing a disposable diaper comprising a liquid permeable topsheet, a liquid impermeable backsheet, and a liquid retentive absorbent member interposed between the two sheets, wherein the disposable diaper has a product basis weight of 50 to 220 g/m$^2$, and a portion of the disposable diaper where the absorbent member is disposed has a part having a rate of body fluid absorption of 3.0 g/sec or more and a part having a saturated body fluid absorption of 75 g/100 cm$^2$ or more (hereinafter referred to as a first invention).

The primary object of the invention is also accomplished by providing a disposable diaper comprising a liquid permeable topsheet, a liquid impermeable backsheet, and a liquid retentive absorbent member interposed between the two sheets, wherein the disposable diaper has a crotch portion, and the crotch portion has a product basis weight of 100 to 450 g/m$^2$, a rate of body fluid absorption of 3.0 g/sec or more, and a saturated body fluid absorption of 60 g/100 cm$^2$ or more (hereinafter referred to as a second invention).

The primary object of the invention is also accomplished by providing a disposable diaper comprising a liquid permeable topsheet, a liquid impermeable backsheet, and a liquid retentive absorbent member interposed between the two sheets, wherein the absorbent member contains a superabsorbent polymer A having a rate of absorption of 8 g/30 sec/0.3 g or more measured by the DW method and a superabsorbent polymer B having a rate of absorption of 5 g/30 sec/0.3 g or less measured by the DW method at a polymer A/polymer B weight ratio of 90/10 to 10/90 and has a fluff pulp content of 0 to 30% by weight (hereinafter referred to as a third invention).

The secondary object of the present invention is accomplished by providing an absorbent article comprising a liquid permeable topsheet, a liquid impermeable backsheet, and a liquid retentive absorbent member interposed between the two sheets, wherein the absorbent member has a fluff pulp content of 0 to 30% by weight, and the thickness of the absorbent article under a load of 180 gf/cm$^2$ and the thickness of the absorbent article after unloading are such that the latter thickness is 1.3 times or greater the former thickness (hereinafter referred to as a forth invention).

BEST MODE FOR CARRYING OUT THE INVENTION

Figure 1:
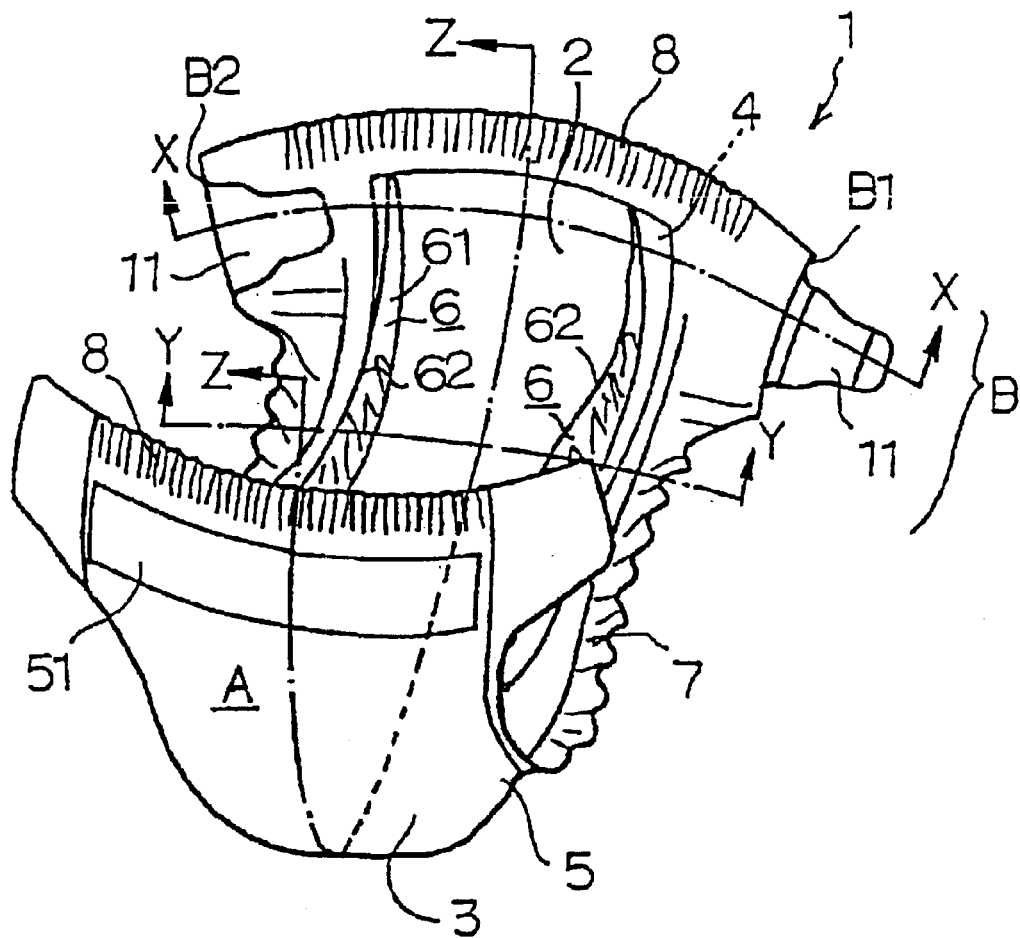
FIG. 1 is a perspective view of a disposable diaper as an embodiment of the present invention.

The present invention will be described hereunder with reference to the preferred embodiments in the practice.

A disposable diaper according to a first embodiment of the present invention, which is one of the embodiments of the first invention, is explained.

As shown in FIGS. 1 through 4, the disposable diaper of the first embodiment has a liquid permeable topsheet 2, a liquid impermeable backsheet 3, and a liquid retentive absorbent member 4 that is interposed between the sheets 2 and 3. Fastening tapes 11 for fastening are provided at both lateral edges B1 and B2 of the rear waist portion B that is positioned at the back side of a wearer. The disposable diaper of this embodiment is of so-called unfolded type.

In detail, the disposable diaper 1 of this embodiment has the absorbent member 4, the backsheet 3 of substantially the same size as the absorbent member 4, and the topsheet 2 which is arranged to cover the surface and the sides of the absorbent member 4 as shown in FIGS. 1 to 4. An outer nonwoven fabric layer 5 is arranged on the back side of the backsheet 3. Water repellent nonwoven fabric 61 is provided on the topsheet 2 on the side of the lateral side portions of the absorbent member 4, with which to form upstanding gathers 6. The outer nonwoven fabric layer 5 and the water repellent nonwoven fabric 61 both extend from each lateral edge of the absorbent member 4 and fixed together, with leg elastic members 71 being held therebetween to form leg gathers 7 on each lateral side. The free end 62 of the water repellent nonwoven fabric 61 is provided with an elastic member 63 to form upstanding gathers 6.

The outer nonwoven fabric layer 5 and the topsheet 2 extend from the longitudinal edges of the disposable diaper 1 to form a pair of waist portions 8. Each waist portion 8 is provided with a waist elastic member 81 having a band form, the elastic member 81 being fixedly sandwiched in between the topsheet 2 and the outer nonwoven fabric layer 5.

The absorbent member 4 is composed of nonwoven fabric 41 holding an absorbent polymer 42 in the interstices among its constituent fibers and supporting paper 43 wrapping the nonwoven fabric 41. Underneath the absorbent member 4 is provided an uneven sheet 44 having compressive recovery properties.

The outer nonwoven fabric layer 5 has on the front waist portion A thereof a landing tape 51 on which the fastening tapes 11 are to be fixed.

The above-described basic structure of the disposable diaper 1 is common to the other disposable diapers according to the embodiments of the second to fourth inventions hereinafter described.

The disposable diaper according to the first embodiment has a product basis weight of 50 to 220 $g/m^2$, preferably 100 to 200 $g/m^2$, and its portion where the absorbent member is disposed has a part having a rate of body fluid absorption of 3.0 g/sec or more, preferably 3.5 g/sec or more, and a part having a saturated body fluid absorption of 75 $g/100$ $cm^2$ or more, preferably 80 $g/100$ $cm^2$ or more.

The expression "the portion (of the disposable diaper) where the absorbent member is disposed" is intended to mean the portion occupied by the absorbent member when the disposable diaper is flatly unfolded and seen in its plan view.

The "product basis weight", "rate of body fluid absorption" and "saturated body fluid absorption" are measured as follows.

Product Basis Weight

A disposable diaper is unfolded flatly, and the area ($m^2$) in this state is measured. The weight (g) of the disposable diaper divided by the area gives the product basis weight ($g/m^2$). In this calculation, the area of the fastening tapes is not included in the product area. In case where the disposable diaper is of pants type, the joint parts between the lateral edges of the rear waist portion and the lateral edges of the front waist portion are separated apart and unfolded flatly, and the product area is measured in this state.

Rate of Body Fluid Absorption

Test pieces of 100 mm by 100 mm are cut out from arbitrary sites of a disposable diaper where the absorbent member is disposed. In case where the width of the absorbent member is narrower than 100 mm, the width of the absorbent member is to be the width of the test piece. Each of the resulting test pieces is placed on a horizontal mount with its topsheet up. An acrylic resin cylinder having an inner diameter of 50 mm is vertically put on the central portion of the test piece, and 50 g of physiological saline is poured into the cylinder all at once. The time required for the physiological saline to soak into the test piece and to disappear from the topsheet is measured, and the amount (g) of physiological saline absorbed per second during the period from addition of physiological saline to disappearance is calculated to obtain the rate of body fluid absorption (g/sec). The expression "the portion of the disposable diaper where the absorbent member is disposed has a part having a rate of body fluid absorption of 3.0 g/sec or more" is intended to mean that one or more of the test pieces cut out from different sites have a rate of body fluid absorption of 3.0 g/sec or more.

Saturated Body Fluid Absorption

Test pieces of 100 mm by 100 mm are cut out from arbitrary sites of a disposable diaper where the absorbent member is disposed. In case where the width of the absorbent member is narrower than 100 mm, the width of the absorbent member is to be the width of the test piece. Each of the resulting test pieces is put in a 150 mm by 150 mm nylon mesh (250 mesh) bag, and the bag is immersed in physiological saline for 1 minute and allowed to drain for 5 minutes. From the weight (g) after drainage, the weight (g) before immersion, and the area ($cm^2$) of the test piece is calculated the absorption (g) of physiological saline per 100 $cm^2$, which is taken as a saturated body fluid absorption ($g/100$ $m^2$). The expression "the portion of the disposable diaper where the absorbent member is disposed has a part having a saturated body fluid absorption of 75 $g/100$ $cm^2$ or more" is intended to mean that one or more of the test pieces cut out from different sites have a saturated body fluid absorption of 75 $g/100$ $cm^2$ or more.

If the product basis weight of a disposable diaper is less than 50 $g/m^2$, which is preferred for lightness and compactness, the diaper easily leaks.

If the portion where an absorbent member is disposed has no part having a rate of body fluid absorption of 3.0 g/sec or more, the diaper easily leaks particularly when a considerable amount of urine is discharged in a short time.

If the portion where an absorbent member is disposed has no part having a saturated body fluid absorption of 75 $g/100$ $cm^2$ or more, the diaper leaks easily where worn for a long time.

In order to secure high resistance to leakage of urine in whichever case where urine rushes out or where much urine is discharged over a long time, it is preferred that both a part having a rate of body fluid absorption of 3.0 g/sec or more (hereinafter referred to as a high-rate absorbing part) and a part having a saturated body fluid absorption of 75 $g/100$ $cm^2$ or more (hereinafter referred to as high-absorption part) be positioned in a urination point portion that corresponds to a wearer's urination point. The term "urination point portion" as used herein denotes the portion containing the urination point of the diaper while worn and its periphery. The high-absorption part and the high-rate absorbing part may be the same part or different parts or overlap with each other.

A disposable diaper according to a second embodiment of the present invention, which is one of the embodiments of the second invention, is explained. The disposable diaper of the second embodiment is basically the same as the first embodiment in constitution so that the explanation given above with regard to the basic constitution applies to the second embodiment.

The crotch portion of the disposable diaper according to the second embodiment has a product basis weight of 100 to 450 g/m² (preferably 200 to 400 g/m²), a rate of body fluid absorption of 3.0 g/sec or more (preferably 3.5 g/sec or more), and a saturated body fluid absorption of 60 g/100 cm² or more (preferably 75 g/100 cm² or more).

Figure 5:
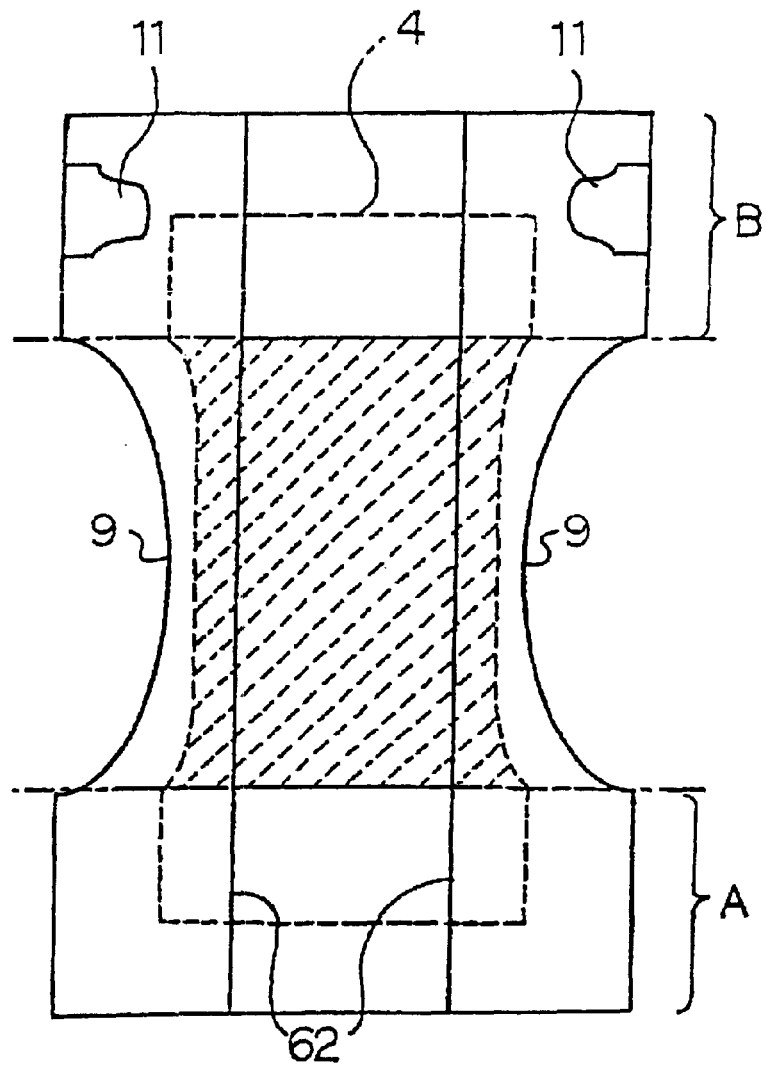
FIG. 5 is a schematic view of the disposable diaper of FIG. 1 in its flatly unfolded state, showing the position of the crotch portion of the diaper.

The term "crotch portion" as used herein designates the portion of the disposable diaper which corresponds to the crotch of a wearer while worn. More definitely, it is the shaded portion of FIG. 5, i.e., the portion in which the absorbent member 4 is disposed and which is between a pair of leg portions 9 corresponding to the periphery of wearer's legs and having an arch shape in the plan view.

The "product basis weight", "rate of body fluid absorption" and "saturated body fluid absorption" of the crotch portion are measured as follows.

Product Basis Weight

A disposable diaper is unfolded flatly, and a 100 mm by 100 mm test piece is cut out of the crotch portion. In case where the width of the absorbent member is narrower than 100 mm, the width of the absorbent member is to be the width of the test piece. Division of the weight (g) of the test piece by the area (m²) of the test piece gives the product basis weight (g/m²). In case where the disposable diaper is of pants type, the joint parts between the lateral edges of the rear waist portion and the lateral edges of the front waist portion are separated apart, the diaper is unfolded flatly, and a test piece is cut out.

Rate of Body Fluid Absorption

A 100 mm by 100 mm test piece is cut out in the same manner as in the measurement of the product basis weight of the crotch portion. The rate of body fluid absorption is measured in the same manner as for the rate of body fluid absorption of the portion where the absorbent member is disposed as described as for the first embodiment, except for using the above prepared test piece.

Saturated Body Fluid Absorption

A 100 mm by 100 mm test piece is cut out in the same manner as in the measurement of the product basis weight of the crotch portion. The saturated body fluid absorption is measured in the same manner as for the saturated body fluid absorption of the portion where the absorbent member is disposed as described with respect to the first embodiment, except for using the above prepared test piece.

If the crotch portion has a product basis weight less than 100 g/m², which is preferred for lightness and compactness, the diaper easily leaks. If the crotch portion has a product basis weight exceeding 450 g/m², it is difficult to obtain light and compact disposable diapers.

If the crotch portion has a rate of body fluid absorption less than 3.0 g/sec, the diaper easily leaks particularly when a considerable amount of urine is discharged in a short time. If the crotch portion has a saturated body fluid absorption less than 60 g/100 cm², the diaper leaks easily where worn for a long time.

In order to secure high resistance to leakage of urine in whichever case where urine rushes out or where much urine is discharged over a long time, it is preferred that the urination point portion, which corresponds to a wearer's urination point, has a rate of absorption of 3.0 g/sec or more and a saturated absorption of 60 g/100 cm² or more.

The product basis weight, rate of body fluid absorption, and saturated body fluid absorption in the first invention can be achieved by reducing the content of fluff pulp in the absorbent member 4 while retaining a high absorption rate and a high saturated absorption by use of a polymer.

Similarly, the product basis weight, rate of body fluid absorption, and saturated body fluid absorption of the crotch portion in the second invention can be accomplished by reducing the content of fluff pulp in the absorbent member 4 while retaining a high absorption rate and a high saturated absorption by use of a polymer.

An absorbent member is made up mainly of an absorbent polymer, a fiber aggregate, and supporting paper wrapping the absorbent polymer and the fiber aggregate. In the first and second embodiments nonwoven fabric 41 having an absorbent polymer 42 held in the fiber interstices thereof is wrapped in supporting paper 43.

The absorbent polymer which can be used in the absorbent member includes conventional known polymers, such as sodium polyacrylate, acrylic acid-vinyl alcohol copolymers, crosslinked sodium polyacrylate, starch-acrylic acid graft copolymers, isobutylene-maleic anhydride copolymers and saponification products thereof, and polyaspartic acid. It is particularly preferred to use a combination of a superabsorbent polymer A having a rate of absorption of 8 g/30 sec/0.3 g or more as measured by the DW method and a superabsorbent polymer B having a rate of absorption of 5 g/30 sec/0.3 g or less as measured by the DW method at a polymer A/polymer B weight ratio of 90/10 to 10/90, with which it is feasible to greatly reduce the fluff pulp compared with ordinary disposable diapers while retaining a high absorption rate and a high saturated absorption.

The absorbent member 4 preferably has a fluff pulp content of from 0 up to 30% by weight for easily making the product basis weight of the diaper 50 to 220 g/m² and for easily making the product basis weight of the crotch portion 100 to 450 g/m². The fluff pulp content can be 0%.

The term "rate of absorption by the DW method (g/30 sec/0.3 g)" means the value of absorption obtained by a method using an apparatus generally known for carrying out the DW method (demand wettability tester), in which, with the liquid levels of physiological saline being equal, 0.3 g of a superabsorbent polymer is scattered on a mount (diameter: 70 mm; No. 1 glass filter having placed thereon No. 2 filter paper), and the water absorption after 30 seconds is gauged by reading the scale on the buret indicating a drop of the liquid level of physiological saline (the water absorption at the time of scattering the polymer is taken zero).

The fiber aggregate used in the absorbent member includes aggregates of fluff pulp; hydrophilic fibers such as rayon fiber, cotton and cellulose acetate; polyolefin fibers, such as polyethylene (PE) and polypropylene (PP); polycondensation fibers, such as polyester and polyamide; and polymers of vinyl monomers such as vinyl chloride and vinyl acetate. These fibers can be used either individually or as conjugate fibers having two or more of them in the form of a laminate or a core/sheath structure. Those which are hydrophobic can be made hydrophilic by treating with a lubricant, etc. Where fiber having heat fusibility is used, the fiber aggregate may be fabricated into nonwoven fabric by heat treatment and the like, which will improve the strength of the absorbent member.

Any supporting paper generally used in disposable diapers can be used with no particular restriction. The uneven sheet 44 may be omitted.

Constituted as described above, the disposable diapers according to the first and second embodiments are light and compact and therefore convenient to carry even when bunched up in a package in which a plurality of the disposable diapers are stacked and compressed. In addition, they have high leakproofness, effectively preventing leakage of urine either in case where urine rushes out or in case where much urine is discharged over a long time.

A disposable diaper according to a third embodiment of the present invention, which is one of the embodiments of the third invention, is explained. The disposable diaper of the third embodiment is basically the same as the first embodiment in constitution so that the explanation given above with regard to the basic constitution of the first embodiment applies to the third embodiment.

The absorbent member 4 of the disposable diaper according to the third embodiment contains a superabsorbent polymer A having a rate of absorption of 8 g/30 sec/0.3 g or more measured by the DW method and a superabsorbent polymer B having a rate of absorption of 5 g/30 sec/0.3 g or less measured by the DW method at a polymer A/polymer B weight ratio of 90/10 to 10/90, preferably 80/20 to 20/80, and has a fluff pulp content of 0 to 30% by weight, preferably 0 to 20% by weight.

If the weight ratio of superabsorbent polymer A to superabsorbent polymer B (A/B) exceeds 90/10, the discharged urine will be fixed in the superabsorbent polymers without diffusing in the absorbent member so that the absorbent member cannot be made full use of, resulting in reduced absorbing performance. On the other hand, if the superabsorbent polymers A/B weight ratio is less than 10/90, it is difficult to reduce fluff pulp, making it difficult to render the disposable diaper light and compact.

Various superabsorbent polymers well-known in the art, such as the above-described superabsorbent polymers, can be used. In the third invention, in particular, those having a rate of absorption of 8 g/30 sec/0.3 g or more by the DW method and those having a rate of absorption of 5 g/30 sec/0.3 g or less by the DW method are selected from among the known superabsorbent polymers and combined at the above-specified weight ratio.

By the combined use of the superabsorbent polymers A and B at the specific ratio, it is feasible to retain a high rate of absorption and a high saturated absorption with a greatly reduced fluff pulp content.

The superabsorbent polymer B preferably has a rate of absorption of 0.5 g/30 sec/0.3 g or more by the DW method. It is preferred for the superabsorbent polymer A to have as high a rate of absorption by the DW method as possible.

The total content of the superabsorbent polymer A and the superabsorbent polymer B in the absorbent member 4 is preferably 50% by weight or more, more preferably 50 to 99% by weight, particularly 60 to 95% by weight.

For obtaining disposable diapers having a high rate of absorption and a high saturated absorption, it is preferred that the superabsorbent polymers A and B be present in the absorbent member in a mutually mixed state.

In the third invention, the absorbent member 4 has a fluff pulp content of 0 to 30% by weight. If the fluff pulp content in the absorbent member is more than 30% by weight, it is difficult to make the disposable diapers significantly lighter and more compact. The fluff pulp content can be 0%.

The absorbent member of the third invention can be made up mainly of for example, an absorbent polymer, a fiber aggregate, and supporting paper in which the former two are wrapped. The relationship between the absorbent polymer and the fiber aggregate is not particularly restricted. In the third embodiment, a mixture of the aforementioned superabsorbent polymers A and B is used as the absorbent polymer 42 as being held in the fiber interstices of the nonwoven fabric 41 as the fiber aggregate.

The fiber aggregate and the supporting paper can be the same as those used in the first and second embodiments.

A disposable diaper according to a fourth embodiment of the present invention, which is one of the embodiments of the fourth invention, is then explained. The disposable diaper of the fourth embodiment is basically the same as the first embodiment in constitution so that the explanation given above with regard to the basic constitution of the first embodiment applies to the fourth embodiment.

The absorbent member of the disposable diaper according to the fourth embodiment has a fluff pulp content of 30% by weight or smaller, preferably 0 to 20% by weight. The thickness of the absorbent article under a load of 180 gf/cm$^2$ and the thickness of the absorbent article after unloading are such that the latter is 1.3 times or greater the former, preferably 1.5 to 3 times (this ratio will hereinafter be referred to as a thickness ratio).

If the fluff pulp content exceeds 30% by weight, the package is not compact. The smaller the fluff pulp content, the preferred for making the absorbent member thinner. This invention includes an embodiment in which no fluff pulp is used, i.e., the fluff pulp content is 0% by weight.

With the above thickness ratio is smaller than 1.3, an easy feeling cannot be secured on use.

The thickness under load and the thickness after unloading are measured according to the following methods.

The absorbent article is unfolded flatly, and a test piece having a width of 100 mm along the lateral direction and a length of 100 mm along the longitudinal direction of the article is cut out, the center of the test piece agreeing with the intersection between a line longitudinally dividing the article into two equal pieces and a line laterally dividing the article into two equal pieces. Where the longitudinal or lateral size of the absorbent article is smaller than 100 mm, the size of the absorbent article is to be the size of the test piece.

The test piece is placed on a horizontal mount and allowed to stand for 24 hours with no load applied. Then, an acrylic resin plate and a weight is put thereon, and the test piece is further allowed to stand under the load for 24 hours. The weight and size of the weight is decided so as to give the test piece a total load of 180 gf/cm$^2$ together with the acrylic resin plate. The acrylic resin plate used was 100 mm wide, 100 mm long, and 5 mm thick.

After 24 hour loading, the thickness of each corner of the test piece under load is measured (measurement 1) to obtain an average thickness of the four corners, which is taken as a thickness under a load of 180 gf/cm$^2$.

The weight and the acrylic resin plate are removed, and the unloaded test piece is left to stand. After 30 minute standing, an acrylic resin plate and a weight giving a total load of 1 gf/cm$^2$ is placed thereon to flatten the test piece because any warpage or distortion of the test piece would prevent accurate thickness measurement. The weight and size of the weight used is decided so as to give the test piece a total load of 1 gf/cm$^2$ together with the acrylic resin plate. The acrylic resin plate used was 100 mm wide, 100 mm long, and 5 mm thick. Immediately after putting the acrylic resin plate and the weight, the thickness of the test piece is measured in the same manner as in the measurement 1, and the average of the measured values is taken as a non-load thickness.

The above-specified thickness ratio can be obtained by, for example, using a cushioning material. In this particular embodiment, the uneven sheet 44 is used as a cushioning material.

The above-described cushioning material preferably has a compressive recovery of 60% or more, particularly 70 to 100%. The compressive recovery is measured as follows.

Before measurement, a cushioning material is allowed to stand for 24 hours to remove any strain that may have been imposed. The strain-free thickness (thickness before compressing the cushioning material) is taken as "a" mm, and the thickness after compressing under a pressure of 180 gf/cm$^2$ for 24 hours followed by removing pressure and allowing it to stand for 30 minutes is taken as "b" mm. The compressive recovery is defined to be b/a. Each thickness is measured in this manner. The term "thickness" as used herein means an average thickness as measured with a laser displacement meter (PA-1830 (trade name), supplied from Keyence Co., Ltd.) in a usual manner.

The cushioning material can be disposed in the upper portion, the lower portion or the inside of the absorbent member. It can be disposed in a plurality of positions. In this particular embodiment, the cushioning material is placed under the absorbent member as shown in FIGS. 2 to 4.

Figure 2:
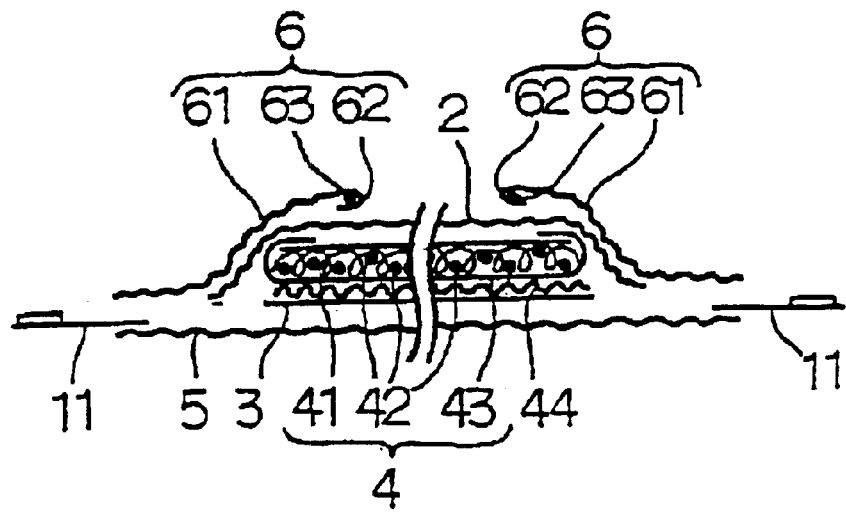
FIG. 2 is a schematic cross section of FIG. 1 taken along line X—X.
Figure 3:
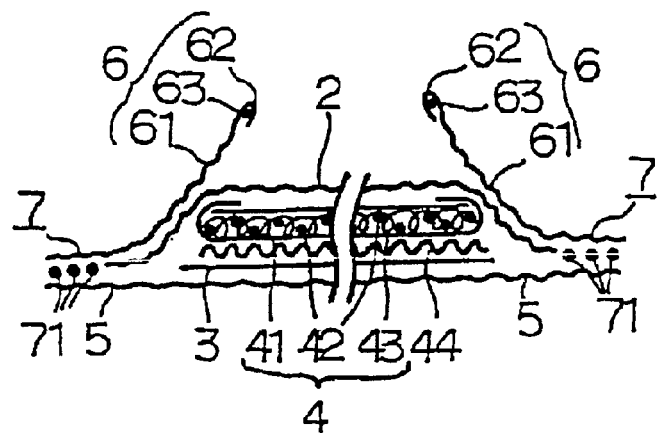
FIG. 3 is a schematic cross section of FIG. 1 taken along line Y—Y.
Figure 4:
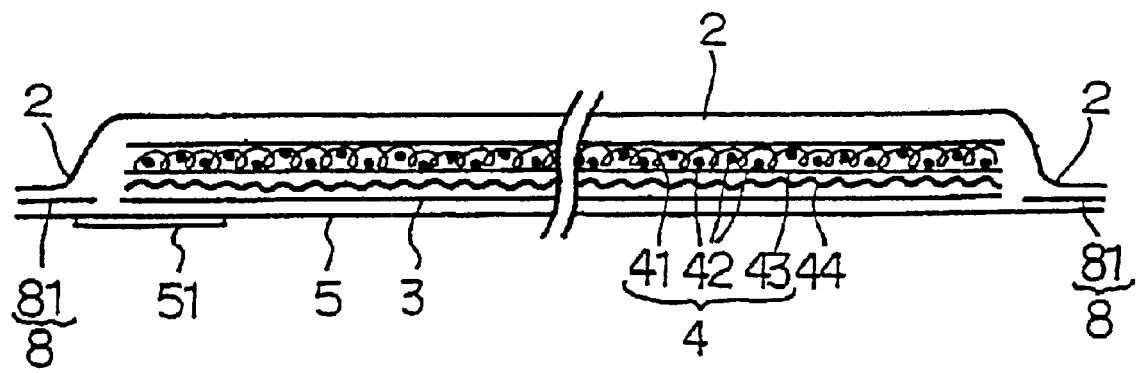
FIG. 4 is a schematic longitudinal section of FIG. 1 taken alone line Z—Z.

While an uneven sheet is used as a cushioning material in this embodiment as shown in FIGS. 2 to 4, an elastic foamed body, such as urethane foam, expanded polyethylene or skeleton foam, is also useful. In addition, film having elasticity or fiber aggregates having elasticity such as nonwoven fabric, woven fabric or knitted fabric, comprising natural rubber or thermoplastic elastomers of styrene, urethane, olefin, ester or metallocene-catalyzed ultra-low-density polyethylene, and the like can also be used. Especially suitable of them are a urethane foam sheet, and a film or fiber aggregate of an ester elastomer or metallocene-catalyzed ultra-low-density polyethylene.

The uneven sheet includes sheets obtained by forming unevenness on the above-described film or fiber aggregate having elasticity by such means as embossing using matched steel rolls. The following uneven sheets 1 and 2 can be mentioned as specific examples.

Uneven Sheet 1: A 2.0 mm thick uneven sheet having compressive recovery properties, which is obtained by embossing a film of ultra-low-density polyethylene (basis weight: 60 g/m$^2$; prepared by polymerization using a metallocene catalyst) through matched steel embossing rolls.

Uneven Sheet 2: A 2.2 mm thick uneven nonwoven fabric sheet having compressive recovery properties, which is obtained by mixing 30% by weight of polyethylene terephthalate (PET)/low-melting elastic PET conjugate fiber (3 denier×51 mm) and 70% by weight of PET fiber (3 denier×51 mm), making a fiber web having a basis weight of 50 g/m$^2$ from the mixed fiber, and embossing the web through matched steel embossing rolls.

The absorbent member can be made up mainly of an absorbent polymer, a fiber aggregate, and supporting paper in which the former two are wrapped. In the fourth embodiment, bulky nonwoven fabric as a fiber aggregate which holds an absorbent polymer in the fiber interstices thereof is wrapped in supporting paper, and the above-mentioned uneven sheet is disposed thereunder to make the absorbent member.

The absorbent polymer, fiber aggregate and supporting paper to be used can be the same as those used in the first to third embodiments. In particular it is preferred to use as an absorbent polymer a combination of the superabsorbent polymers A and B as used in the third invention in the specific ratio, which is preferred for retaining high absorbing performance even where the fluff pulp content is greatly reduced to 30% by weight or less as compared with ordinary diapers as described above to make a package of diapers compact. Depending on the kind and amount of the absorbent polymers, fluff pulp may be omitted.

The materials forming each constituent member of the disposable diapers according to the first to fourth embodiments are described hereunder. The topsheet, backsheet, water repellent nonwoven fabric and outer nonwoven fabric layer can be of any materials generally employed in disposable diapers without particular restriction.

The elastic members for the leg portions, upstanding gathers and waist portions can be of any materials generally used in disposable diapers with no particular restriction.

Materials for forming the fastening tapes include tape coated with an adhesive and a male member of mechanical fastener. As the landing tape, tape having a release finish, which is combined with tape coated with an adhesive as a fastening tape, and a female member of a general mechanical fastener, which is combined with a male member, can be used with no particular limitation.

Constituted as described above, the disposable diaper of the third embodiment is light and compact. Where a plurality of the disposable diapers are packed in a packaging bag as stacked and compressed, they are light and compact and therefore easy to carry. Moreover, they have high leakproofness, effectively preventing leakage of urine either in case where urine rushes out or in case where much urine is discharged over a long time.

Constituted as described above, the disposable diaper of the fourth embodiment can be made thinner and more compact when packaged. Upon being taken out of the package, the diaper restores its thickness moderately so that it can be used at ease without giving a user, etc. feelings of unease about the thinness.

While the above embodiments of the practice have been described with particular reference to unfolded type disposable diapers intended for babies, the first to third invention are also applicable to pants type disposable diapers intended for babies and unfolded or pants type disposable diaper for adults.

The fourth invention is applicable to sanitary napkins, incontinence pads, etc. as well as unfolded or pants type disposable diapers.

The absorbent member used in the third embodiment is suitable as, other than the absorbent member of disposable diapers, the absorbent member of absorbent articles used for absorbing body fluids, such as sanitary napkins, incontinence pads and panty liners. In addition, it is usable as the absorbent member of drip sheets, kitchen paper towels, household cleaning sheets, undersheets for pet animals and the like.

Particulars that have been described with respect to a certain embodiment could apply to other embodiments. Therefore particulars of an embodiment that have not been described above could be understood from the corresponding description of other embodiments. The particulars of the embodiments are exchangeable among them.

The present invention will now be illustrated in greater detail by way of Examples, but it should be understood that the present invention is not construed as being limited thereto.

EXAMPLE 1

A superabsorbent polymer A having a rate of absorption of 11.8 g/30 sec/0.3 g by the DW method (10SH-P (trade name), available from Sumitomo Seika Chemicals Co., Ltd.) and a superabsorbent polymer B having a rate of absorption of 3.6 g/30 sec/0.3 g by the DW method (CA-W4 (trade name), available from Nippon Shokubai Co., Ltd.) were mixed at a polymer A/polymer B weight ratio of 50/50 to prepare a mixed superabsorbent polymer. PP/PE core/sheath conjugate fiber and PET fiber were mixed at a weight ratio of 70/30 and fabricated into airthrough nonwoven fabric having a basis weight of 30 g/m². The mixed superabsorbent polymer was scattered on the nonwoven fabric in an amount of 200 g/m² to be held in the interstices of the fibers. A tissue having a basis weight of 15 g/m² was wrapped about the nonwoven fabric having the polymers held therein to make an absorbent member.

A PP/PE nonwoven fabric was put on one side of the absorbent member as a topsheet, and on the other side was put a PE film as a backsheet. Known fastening tapes, waist elastic members, leg elastic members, and the like were provided to obtain a medium size disposable diaper for babies having the form shown in FIG. 1.

EXAMPLE 2

A hot-melt adhesive was applied to a tissue, and the mixed superabsorbent polymer prepared in the same manner as in Example 1 was scattered thereon in an amount of 200 g/m². Another tissue having a hot-melt adhesive applied thereto was superposed thereon to make an absorbent member. A disposable diaper was obtained by using the resulting absorbent member in the same manner as in Example 1.

Comparitive Example 1

A superabsorbent polymer having a rate of absorption of 3.6 g/30 sec/0.3 g by the DW method (CA-W4 (trade name), supplied from Nippon Shokubai) and fluff pulp were mixed at a polymer/pulp weight ratio of 40/60 and built up into a sheet having 200 g/m² of the superabsorbent polymer and 300 g/m² of the fluff pulp. A tissue having a basis weight of 15 g/m² was wrapped about the sheet to make an absorbent member.

A disposable diaper was obtained by using the resulting absorbent member in the same manner as in Example 1.

Comparitive Example 2

The same superabsorbent polymer as used in Comparative Example 1 and fluff pulp were mixed at the same mixing ratio as in Comparative Example 1, and the mixture was built up into a sheet having 80 g/m² of the superabsorbent polymer and 120 g/m² of the fluff pulp. A tissue having a basis weight of 15 g/m² was wrapped about the sheet to make an absorbent member.

A disposable diaper was obtained by using the resulting absorbent member in the same manner as in Example 1.

The weight, product basis weight, rate of absorption and saturated absorption of the disposable diapers obtained in Examples 1 and 2 and Comparative Examples 1 and 2 were measured. The results obtained are shown in Table 1 below.

In every disposable diaper tested, the test piece taken from the urination point portion, which corresponds to the urination point of a wearer, displayed the highest rate of absorption and the highest saturated absorption of all the test pieces. Therefore, the rate of absorption and the saturated absorption shown in Table 1 are those of the test piece taken from the urination point portion.

Further, the product basis weight, rate of absorption, and saturated absorption of the crotch portion of each disposable diaper were measured in accordance with the aforementioned methods. In Table 2 are shown the results of measurement together with the weight of the whole diaper.

Figure 6:
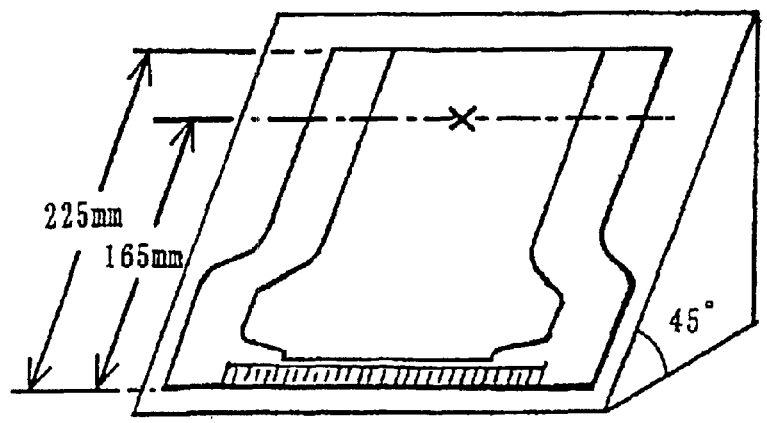
FIG. 6 is an illustration showing the method of evaluating absorbing performance (maximum absorption) of a disposable diaper.

The absorbing performance (the maximum absorption) of each disposable diaper was evaluated as follows. The disposable diaper was cut at 225 mm wide of the edge of the front waist portion to make a test piece. The test piece was put on a slant mount having an incline of 45° with the edge of the waist portion down as shown in FIG. 6. Portions of physiological saline each measuring 40 ml were poured into a position 165 mm from the edge of the waist portion at a rate of S ml/sec each at 5 minute intervals. The maximum amount of physiological saline that could be retained by the absorbent member is shown in Tables 1 and 2. The fluff pulp content (wt %) in the disposable diapers of Examples 1 and 2 and Comparative Examples 1 and 2 were 0%, 0%, 57%, and 52%, respectively.

TABLE 1

|  | Diaper Weight (g) | Basis Weight (g/m²) | Absorption Rate (g/sec) | Saturated Absorption (g/100 cm²) | Maximum Absorption (g) |
| --- | --- | --- | --- | --- | --- |
| Example 1 | 25 | 192 | 3.7 | 100 | 160 |
| Example 2 | 24 | 185 | 3.2 | 94 | 160 |
| Compara. Example 1 | 40 | 308 | 3.5 | 98 | 160 |
| Compara. Example 2 | 24 | 185 | 2.6 | 41 | 80 |

TABLE 2

|  | Diaper Weight (g) | Basis Weight of Crotch Portion (g/m²) | Absorption Rate (g/sec) | Saturated Absorption (g/100 cm²) | Maximum Absorption (g) |
| --- | --- | --- | --- | --- | --- |
| Example 1 | 25 | 340 | 3.7 | 100 | 160 |
| Example 2 | 24 | 316 | 3.2 | 94 | 160 |
| Compara. Example 1 | 40 | 610 | 3.5 | 98 | 160 |
| Compara. Example 2 | 24 | 310 | 2.6 | 41 | 80 |

The disposable diapers of Examples 1 and 2, which belong to the first and the second inventions, weigh 25 g or less each, being significantly lighter than conventional diapers and nevertheless maintain high leakproof performance. Although the disposable diaper of Comparative Example 1 has high leakproof performance, it is heavy and inconvenient to carry when a plurality of the disposable diapers are combined in a package. The disposable diaper of Comparative Example 2 corresponds to that of Comparative Example 1 from which the fluff pulp and the superabsorbent polymer making up the absorbent member are cut down by 60%. It is light but inferior in resistance to leakage.

EXAMPLE 3

The superabsorbent polymers A and B used in Example 1 were mixed at a polymer A/polymer B weight ratio of 30/70 to prepare a mixed superabsorbent polymer.

The mixed superabsorbent polymer, fluff pulp and heat-fusible PP/PE core/sheath conjugate fiber were mixed up at a weight ratio of 85/10/5 and built up into a sheeting having 200 g/m² of the mixed superabsorbent polymer, 24 g/m² of fluff pulp, and 12 g/m² of the heat-fusible conjugate fiber. The resulting fiber aggregate was Wrapped in a tissue having a basis weight of 15 g/m² and subjected to a heat treatment to make an absorbent member having a fluff content of 9% by weight.

A medium size disposable diaper for babies having the form of FIG. 1 was prepared in the same manner as in Example 1, except for using the above prepared absorbent member.

EXAMPLE 4

The superabsorbent polymers A and B used in Example 3 were mixed at a polymer A/polymer B weight ratio of 50/50 to prepare a mixed superabsorbent polymer. The resulting mixed superabsorbent polymer was scattered on a tissue having a hot-melt adhesive applied thereto in an amount of 200 g/m², and a fluff pulp web having a basis weight of 80 g/m² was put thereon. A tissue having a hot-melt adhesive applied was superposed on the fluff pulp web to make an absorbent member. The fluff pulp content of the absorbent member was 26% by weight. A disposable diaper was prepared in the same manner as in Example 3, except for using the resulting absorbent member.

The following measurement was made on the disposable diapers prepared in Examples 3 and 4. The weight and the product basis weight of the diaper itself were measured in accordance with the methods described in regard to the first embodiment. Rate of body fluid absorption and saturated body fluid absorption of the crotch portion were measured according to the methods described with regard to the second embodiment.

The absorbing performance of the disposable diapers of Examples 3 and 4 was evaluated in terms of maximum absorption in accordance with the method shown in FIG. 6.

The results of these measurements are shown in Table 3 below.

TABLE 3

| | Diaper Weight (g) | Basis Weight (g/m²) | Absorption Rate (g/sec) | Saturated Absorption (g/100 cm²) | Maximum Absorption (g) |
|---|---|---|---|---|---|
| Example 3 | 25 | 192 | 3.7 | 100 | 160 |
| Example 4 | 28 | 215 | 3.8 | 102 | 160 |
| Compara. Example 1 | 40 | 308 | 3.5 | 98 | 160 |
| Compara. Example 2 | 24 | 185 | 2.6 | 41 | 80 |

The disposable diapers of Examples 3 and 4, which belong to the third invention, weigh less than 30 g each, being significantly lighter than conventional diapers and yet maintain high leakproof performance. Although the disposable diaper of Comparative Example 1 has high leakproof performance owing to the high fluff pulp content in its absorbent member, it is heavy and inconvenient to carry when a plurality of the disposable diapers are combined in a package. The disposable diaper of Comparative Example 2 corresponds to that of Comparative Example 1 from which the fluff pulp and the superabsorbent polymer making up the absorbent member are cut down by 60%. It is light but inferior in resistance to leakage.

The high leakproof performance of the disposable diapers according to the third invention (Examples 3 and 4) for their lightness is considered to owe to the superabsorbent polymer having a rate of absorption of 8 g/30 sec/0.3 g or more by the DW method which carries out the function conventionally performed by fluff pulp in quickly taking discharged urine into the inside of the absorbent member.

EXAMPLE 5

Disposable diapers having the form shown in FIG. 1 were fabricated from known members, except for using cushioning materials whose thickness and compressive recovery are shown in Table 4. The thickness under load and no-load thickness of the resulting diapers were measured. The results obtained are shown in Table 4.

TABLE 4

| | Cushioning Material | | | Diaper | | |
|---|---|---|---|---|---|---|
| Sample No. | Kind | Thickness* (mm) | Compressive Recovery (%) | Thickness under Load (mm) | No-load Thickness (mm) | Thickness Ratio |
| 1 | uneven sheet 1 | 2.0 | 86 | 2.5 | 4.2 | 1.68 |
| 2 | uneven sheet 2 | 2.2 | 83 | 2.8 | 4.6 | 1.64 |
| 3 | urethane foam | 2.3 | 99 | 3.0 | 5.3 | 1.77 |
| 4 | skeleton foam | 2.5 | 98 | 3.2 | 5.6 | 1.75 |

Note:
*Initial thickness with no load applied.

INDUSTRIAL APPLICABILITY

The first to third inventions provide disposable diapers which are light and compact and therefore convenient to carry around even when a plurality of the diapers are put in a package and also which are excellent in leakproofness.

The fourth invention provides absorbent articles, such as disposable diapers, which are compact in a package but restore thickness when taken out of the package to make a user feel at ease while in use. Further, the absorbent articles of the fourth invention have cushioning to provide a good fit to a wearer on being put on.

This application claims the priority of Japanese Patent Application Nos. 11-104626, 11-104627, 11-104628 each filed Apr.12, 1999 and Japanese Patent Application No. 11-134310 filed May 14, 1999, which are incorporated herein by reference.

What is claimed is:

1. An absorbent member comprising, in admixture, a superabsorbent polymer A having a rate of absorption of 8 g/30 sec/0.3 g or more measured by Demand Wettability DW method and a superabsorbent polymer B having a rate of absorption of 0.5 g/30 sec/0.3 g to 5 g/30 sec/0.3 g measured by DW method at a polymer A/polymer B weight ratio of 90/10 to 10/90, said admixture optionally further comprising fluff pulp in an amount of from 0 to 30 % by weight.

2. An absorbent member according to claim 1, wherein the total content of the superabsorbent polymer A and the superabsorbent polymer B in said absorbent member is 50% by weight or more.

3. A disposable diaper comprising a liquid permeable topsheet, a liquid impermeable backsheet, and a liquid retentive absorbent member interposed between the topsheet and said backsheet, wherein said absorbent member comprises, in admixture, a superabsorbent polymer A having a rate of absorption of 8 g/30 sec/0.3 g or more measured by Demand Wettability DW method and a superabsorbent polymer B having a rate of absorption of 0.5 g/30 sec/0.3 g to 5 g/30 sec/0.3 g measured by DW method at a polymer A/polymer B weight ratio of 90/10 to 10/90, said admixture optionally further comprising fluff pulp in an amount of from 0 to 30% by weight.

4. An absorbent article comprising a liquid permeable topsheet, a liquid impermeable backsheet, and a liquid retentive absorbent member interposed between said topsheet and said backsheet, wherein said absorbent member has a fluff pulp content of 0 to 30% by weight, and the ratio of the thickness of an unloaded absorbent article is at least 1.3 times the thickness of said absorbent article under a load of 180 gf/cm$^2$, and wherein said absorbent member comprises, in admixture, a superabsorbent polymer A having a rate of absorption of 8 g/30 sec/0.3 g or more measured by Demand Wettability DW method and a superabsorbent polymer B having a rate of absorption of 0.5 g/30 sec/0.3 g to 5 g/30 sec/0.3 g measured by DW method at a polymer A/polymer B weight ratio of 90/10 to 10/90.

5. An absorbent article according to claim 2, wherein the total content of the superabsorbent polymer A and the superabsorbent polymer B in said absorbent member is 60 to 95% by weight.

6. An absorbent article according to claim 4, wherein the total content of the superabsorbent polymer A and the superabsorbent polymer B in said absorbent member is 60 to 95% by weight.

* * * * *